US005728674A

United States Patent [19]
Sprecher et al.

[11] Patent Number: 5,728,674
[45] Date of Patent: Mar. 17, 1998

[54] INHIBITION OF BLOOD COAGULATION BY HUMAN-KUNITZ-TYPE INHIBITORS

[75] Inventors: Cindy A. Sprecher, Seattle, Wash.; Walt Kisiel, Albuquerque, N. Mex.; Donald C. Foster, Seattle, Wash.

[73] Assignee: ZymoGenetics, Inc., Seattle, Wash.

[21] Appl. No.: 458,090

[22] Filed: Jun. 1, 1995

Related U.S. Application Data

[62] Division of Ser. No. 147,710, Nov. 5, 1993, Pat. No. 5,455,338.

[51] Int. Cl.$^6$ .......................... A61K 38/16; A61K 38/17; A61K 38/36
[52] U.S. Cl. .......................... 514/2; 435/69.1; 435/172.3; 514/8; 530/300; 530/350
[58] Field of Search .................. 435/69.1, 172.3, 435/810; 436/501; 514/2–14; 530/300, 350; 935/77, 78

[56] References Cited

U.S. PATENT DOCUMENTS

| | | | |
|---|---|---|---|
| 4,736,018 | 4/1988 | Reutelingsperger | 530/381 |
| 5,106,833 | 4/1992 | Broze, Jr. et al. | 514/12 |
| 5,276,015 | 1/1994 | Khouri et al. | 514/12 |
| 5,312,736 | 5/1994 | Rasmusson et al. | 435/69.2 |

FOREIGN PATENT DOCUMENTS

| | | |
|---|---|---|
| 0 318 451 | 5/1989 | European Pat. Off. . |
| 93/14121 | 7/1993 | WIPO . |
| 93/14122 | 7/1993 | WIPO . |

OTHER PUBLICATIONS

Sprecher et al., *Proc. Natl. Acad. Sci. U.S.A.* 91:3353–3357, 1994.
Kisiel, *Blood* 84(12): 4384, 1994.
Miyagi et al., *J. Biochem.* 116: 939–942, 1994.
Day et al., *Thrombosis Research* 68: 369–381, 1992.
Girard et al., *Nature* 338: 518–520, 1989.
Hamamoto et al., *J. Biol. Chem.* 268(2): 8704–8710, 1993.
Enjyoji et al., *J. Biochem.* 111: 681–687, 1992.
Broze, Jr., et al. *Biochemistry* 29(33): 7539–7546, 1990.
Wun et al., *J. Biol. Chem.* 263(13): 6001–6004, 1988.
Broze, Jr., et al., *Blood* 71(2): 335–343, 1988.
Pedersen et al., *J. Biol.* 265(28): 16786–16793, 1990.
Warn–Cramer et al., *Circulation* 74(Supp II) Abstract No. 1630: II–408, 1986.
Norris et al., *Biol., Chem. Hoppe–Seyler 371:* 37–42, 1990.
Nordfang et al., *Biochemistry* 30: 10371–10376, 1991.
Wesselschmidt et al., *Blood* 79(8): 2004–2010, 1992.
Girard et al., *Science* 248: 1421–1424, 1990.
Sanders, et al., *Blood* 66(1): 204–212, 1985.
Broze, Jr., et al., *Proc. Natl. Acad. Sci. U.S.A.* 84: 1886–1890, 1987.
Warn–Cramer et al., *Thrombosis and Haemostasis* 60(3): 453–456, 1988.
Wesselschmidt et al., *Nucleic Acids Research* 18(21): 6440, 1990.
Day et al., *Blood* 76(8): 1538–1545, 1990.
Neuenschwander et al., *J. Biol. Chem.* 267(20): 14477–14482, 1992.
Broze et al., *Blood* 69(1): 150–155, 1987.
Adams et al., *Nature* 355: 632–634, 1992.
Laskowski et al., *Ann. Rev. Biochem.* 49: 593–626, 1980.
Creighton et al., *J. Mol. Biol.* 194: 11–22, 1987.
Butzow et al., *Biochemical and Biophysical Communications* 150(1): 483–490, 1988.

*Primary Examiner*—Ardin H. Marschel
*Attorney, Agent, or Firm*—Susan E. Lingenfelter

[57] ABSTRACT

The present invention provides isolated DNA molecules comprising a DNA segment encoding novel human Kunitz-type inhibitors. Also provided are DNA constructs comprising a first DNA segment encoding a novel human Kunitz-type inhibitor wherein said first DNA segment is operably linked to additional DNA segments required for the expression for the first DNA segment, as well as host cells containing such DNA constructs and methods for producing proteins from the host cells.

3 Claims, No Drawings

INHIBITION OF BLOOD COAGULATION BY HUMAN-KUNITZ-TYPE INHIBITORS

This is a division of application Ser. No. 147,710, filed Nov. 5, 1993, now issued as U.S. Pat. No. 5,455,338.

BACKGROUND OF THE INVENTION

Blood coagulation is a process consisting of a complex interaction of various blood components, or factors, which eventually gives rise to a fibrin clot. Generally, the blood components that participate in what has been referred to as the coagulation "cascade" are proenzymes or zymogens, enzymatically inactive proteins that are converted to proteolytic enzymes by the action of an activator, itself an activated clotting factor. Coagulation factors that have undergone such a conversion are generally referred to as "active factors," and are designated by the addition of a lower case postscript "a" (e.g., factor VIIa).

Two systems promote blood clotting and thereby participate in normal hemostasis. These systems have been referred to as the "intrinsic" and the "extrinsic" coagulation pathways. It is now believed that the intrinsic pathway plays a role in the growth and maintenance of fibrin formation and that the "extrinsic" pathway is an overlapping mechanism that is critical for the initiation of fibrin formation. The pathways converge at the activation of factor X to Xa and proceed through a "common" pathway to fibrin formation. After vascular injury, tissue factor initiates the "extrinsic" coagulation pathway by complexing with factor VII in a calcium-dependent manner to facilitate the conversion of factor VII to VIIa. The factor VIIa-tissue factor complex can directly activate factor X to Xa. The intrinsic pathway may be activated by the generation of thrombin or factor XIIa which cleaves factor XI to generate factor XIa, the required enzyme for the initiation of the "intrinsic" coagulation cascade.

Fibrin formation via the "extrinsic" pathway is controlled by the presence of tissue factor pathway inhibitor protein (TFPI) which regulates the pathway in a factor Xa-dependent manner. TFPI, a multivalent Kunitz-type inhibitor, is believed to regulate the extrinsic pathway by forming a quaternary complex with factor Xa, tissue factor and factor VIIa, thus inhibiting the formation of free factor Xa and factor VIIa (Broze et al., *Biochemistry* 29: 7539–7546, 1990; which is incorporated by reference herein in its entirety).

in some instances, for example, kidney dialysis, deep vein thrombosis, and disseminated intravascular coagulation (DIC), it is necessary to block the coagulation cascade through the use of anticoagulants, such as heparin, coumarin, derivatives of coumarin, indandione derivatives, or other agents. A heparin treatment or an extracorporeal treatment with citrate ion (U.S. Pat. No. 4,500,309) may, for example, be used in dialysis to prevent coagulation in the course of treatment. Heparin is also used in preventing deep vein thrombosis in patients undergoing surgery. Treatment with low doses of heparin may, however, cause heavy bleeding. Furthermore, because heparin has a half-life of approximately 80 minutes, it is rapidly cleared from the blood. Because heparin acts as a cofactor for antithrombin III (AT III), and antithrombin III is rapidly depleted in DIC treatment, it is often difficult to maintain the proper heparin dosage, necessitating continuous monitoring of AT III and heparin levels. Heparin is also ineffective if AT III depletion is extreme. Further, prolonged use of heparin may increase platelet aggregation, reduce platelet count, and has been implicated in the development of osteoporosis. Indandione derivatives may also have toxic side effects.

In addition to the anticoagulants briefly described above, there are a variety of compositions disclosed within the art that are alleged to have anticoagulant activity. One such composition is disclosed by Reutelingsperger et al. (*Eur. J. Biochem.* 151: 625–629, 1985) who isolated a 32,000 dalton polypeptide from human umbilical cord arteries. Another composition is disclosed by Warn-Cramer et al. (*Circulation* Suppl, part 2, 74: 2-408ii, Abstract #1630, 1986). They detected a factor VIIa inhibitor of an apparent molecular weight of 34,500 in plasma.

Protein inhibitors are classified into a series of families based on extensive sequence homologies among the family members and the conservation of intrachain disulfide bridges (for review, see Laskowski and Kato, *Ann. Rev. Biochem.* 49: 593–626, 1980). Serine protease inhibitors of the Kunitz family are characterized by their homology with aprotinin (bovine pancreatic trypsin inhibitor). Aprotinin is known to inhibit various serine proteases including trypsin, chymotrypsin, plasmin and kallikrein. Kunitz-type inhibitor domains have been reported in larger proteins such as the inter-α-trypsin inhibitors (Hochstrasser et al., *Hoppe-Seylers Z. Physiol. Chem.* 357: 1659–1661, 1969 and Tschesche et al., *Eur. J. Biochem.* 16: 187–198, 1970), the β-amyloid protein precursor and the $\alpha_3$-collagen type VI (Chu et al., *EMBO J.* 9: 385–393, 1990). TFPI (also known as extrinsic pathway inhibitor (EPI) or lipoprotein-associated coagulation inhibitor (LACI)) is a plasma protease inhibitor that consists of three tandem Kunitz-type inhibitors flanked by a negatively charged amino terminus and a positively charged carboxyl terminus. The first and second Kunitz-type domains have been shown to inhibit factor VIIa and factor Xa activity, respectively.

There is still a need in the art for improved compositions having anticoagulant activity that do not produce the undesirable side effects associated with traditional anticoagulant compositions. The present invention fulfills this need, and further provides other related advantages.

It is therefore an object of the present invention to provide novel human protease inhibitors of the Kunitz family of inhibitors with similar inhibitor profiles for use as anticoagulants and in the treatment of deep vein thrombosis and DIC.

SUMMARY OF THE INVENTION

Briefly stated, the present invention provides DNA molecules which comprise a DNA segment encoding a Kunitz-type inhibitor, wherein the DNA segment comprises the sequence of nucleotides of SEQ ID NO:14 from 1 to 165, wherein each nucleotide triplet 1 to 3, 4 to 6, 160 to 162 and 163 to 165 individually encodes any amino acid except cysteine. Within one aspect of the invention, the Kunitz-type inhibitor comprises the sequence of nucleotides of SEQ ID NO:1 from nucleotide 138 to nucleotide 305. Within another aspect of the invention, the Kunitz-type inhibitor comprises the sequence of nucleotides of SEQ ID NO:1 from nucleotide 39 to nucleotide 743. Within another aspect, the Kunitz-type inhibitor comprises the sequence of nucleotides of SEQ ID NO:1 from nucleotide 138 to nucleotide 493. Within yet another aspect of the invention, the Kunitz-type inhibitor comprises the sequence of nucleotides of SEQ ID NO:1 from nucleotide 138 to nucleotide 671.

Within one aspect of the invention, the DNA segment encodes a Kunitz-type inhibitor comprising the amino acid sequence of SEQ ID NO:15 wherein each Xaa is individually any amino acid except cysteine. Within one aspect of the invention, the DNA segment encodes a Kunitz-type inhibitor comprising the amino acid sequence of SEQ ID NO:2 from glutamic acid, amino acid number 34 to isoleucine, amino acid number 89. Within another aspect of the invention, the DNA segment encodes a Kunitz-type inhibitor comprising the amino acid sequence of SEQ ID NO:2 from Met, amino acid 1 to Phe, amino acid number 235. Within another aspect of the invention, the DNA segment encodes a Kunitz-tyPe inhibitor comprising the amino acid sequence of SEQ ID NO:2 from glutamic acid, amino acid number 34 to lysine, amino acids 152. Within yet another aspect of the invention, the DNA segment encodes a Kunitz-type inhibitor comprising the amino acid sequence of SEQ ID NO:2 from glutamic acid, amino acid number 34 to alanine, amino acid number 211.

The present invention also provides DNA constructs comprising a first DNA segment encoding a human Kunitz-type inhibitor operably linked to additional DNA segments necessary for the expression of the first DNA segment, host cells containing such DNA constructs, as well as methods for producing a human Kunitz-type inhibitor comprising the step of culturing a host cell and isolating said Kunitz-type inhibitor.

Within another aspect of the invention, isolated Kunitz-type inhibitors are provided- Within another embodiment, an isolated human Kunitz-type inhibitor comprises the amino acid sequence of SEQ ID NO:15 wherein each Xaa is individually any amino acid except cysteine. Within one aspect of the invention, the Kunitz-type inhibitor comprises the amino acid sequence of SEQ ID NO:2 from Met, amino acid 1 to Phe, amino acid number 235; the amino acid sequence of SEQ ID NO:2 from glutamic acid, amino acid number 34, to isoleucine, amino acid number 89; the amino acid sequence of SEQ ID NO:2 from glutamic acid, amino acid number 34 to lysine, amino acid number 152 or the amino acid sequence of SEQ ID NO:2 from glutamic acid, amino acid number 34 to alanine, amino acid number 211. Within another aspect of the invention, the Kunitz-type inhibitor further comprises the amino acid sequence of SEQ ID NO:12 or SEQ ID NO:13 at its amino-terminus.

Within another aspect of the invention, isolated antibodies are provided which specifically bind to a human Kunitz-type inhibitor. Within one embodiment, the antibody is a monoclonal antibody.

Within yet another aspect of the invention, a pharmaceutical composition is provided which comprises the amino acid sequence of SEQ ID NO:15 wherein each Xaa is individually any amino acid except cysteine. Within one aspect of the invention, the pharmaceutical composition comprises a human Kunitz-type inhibitor comprising the amino acid sequence of SEQ ID NO:2 from Met, amino acid 1 to Phe, amino acid number 235; the amino acid sequence of SEQ ID NO:2 from glutamic acid, amino acid number 34, to isoleucine, amino acid number 89; the amino acid sequence of SEQ ID NO:2 from glutamic acid, amino acid number 34 to lysine, amino acid number 152 or the amino acid sequence of SEQ ID NO:2 from glutamic acid, amino acid number 34 to alanine, amino acid number 211.

Within yet another aspect of the invention, a method for inhibiting blood coagulation in a mammal is disclosed comprising administering a human Kunitz inhibitor, comprising the amino acid sequence of SEQ ID NO:15 wherein each Xaa is individually any amino acid except cysteine, in an amount sufficient to inhibit blood coagulation. Within another aspect of the invention, a method for inhibiting blood coagulation in a mammal is disclosed in which a Kunitz-type inhibitor comprises the amino acid sequence of SEQ ID NO:2 from methionine, amino acid 1 to phenylalanine, amino acid number 235; the amino acid sequence of SEQ ID NO:2 from glutamic acid, amino acid number 34 to isoleucine, amino acid number 89; the amino acid sequence of SEQ ID NO:2 from glutamic acid, amino acid number 34 to lysine, amino acids 152 or the amino acid sequence of SEQ ID NO:2 from glutamic acid, amino acid number 34 to alanine, amino acid number 211 is administered in an amount sufficient to inhibit blood coagulation. In yet another aspect of the invention, a method for inhibiting blood coagulation in a mammal is provided in which a Kunitz-type inhibitor further comprises the amino acid sequence of SEQ ID NO:12 or SEQ ID NO:13 at its amino-terminus, is administered in an amount sufficient to inhibit blood coagulation.

Within another aspect of the invention, probes of at least 12 nucleotides are provided, wherein the probes are capable of hybridizing with nucleic acids encoding a Kunitz-type inhibitor domain comprising the nucleotide sequence of SEQ ID NO:1, nucleotide variants of SEQ ID NO:1, or DNA segments encoding DNA sequences complementary to SEQ ID NO:1 or its variants.

These and other aspects will become evident upon reference to the following detailed description.

DETAILED DESCRIPTION OF THE INVENTION

The present invention provides novel human Kunitz-type inhibitors. One advantage of the inhibitors of the present invention is that they inhibit factor VIIa in the absence of factor Xa, and thus do not require production of factor Xa via the intrinsic or extrinsic pathway. More particularly, the present invention provides a novel, previously unknown Kunitz-type inhibitor that shares amino acid sequence homology and overall domain organization with tissue factor pathway inhibitor (TFPI). This novel Kunitz-type inhibitor has been designated TFPI-2.

Among the features of the present invention are isolated DNA molecules encoding novel human Kunitz-type inhibitors. Such isolated molecules are those that are separated from their natural environment and include cDNA and genomic clones. Isolated DNA molecules of the present invention are provided free of other genes with which they are naturally associated and may include naturally occurring 5' and 3' untranslated sequences that represent regulatory regions such as promoters and terminators. The identification of regulatory regions within the naturally occurring 5' and 3' untranslated regions will be evident to one of ordinary skill in the art (for review, see Dynan and Tijan, *Nature* 316: 774–778, 1985; Birnstiel et al., *Cell* 4: 349–359, 1985; Proudfoot, *Trends in Biochem. Sci.* 14: 105–110, 1989; and Sambrook et al., *Molecular Cloning: A Laboratory Manual*, Second Edition, Cold Spring Harbor, N.Y., 1989; which are incorporated herein by reference).

The isolated DNA molecules of the present invention are useful in producing recombinant human Kunitz-type inhibitors. Thus, the present invention provides the advantage that human Kunitz-type inhibitors are produced in high quantities that may be readily purified using methods known in the art (see generally, Scopes, Protein purification, Springer-Verlag, N.Y., 1982). Alternatively, the proteins of the present invention may be synthesized following conventional synthesis methods such as by the solid-phase synthesis such as the method of Barany and Merrifield (in *The Peptides.*

*Analysis, Synthesis, Biology* Vol. 2, Gross and Meienhofer, eds., Academic Press, N.Y., pp. 1–284, 1980), by partial solid-phase techniques, by fragment condensation or by classical solution addition.

Thus, an additional feature of the present invention is an isolated human Kunitz-type inhibitor. Isolated proteins and peptides of the present invention are proteins of at least about 50% homogeneity, more preferably of 70% to 80% homogeneity with a protein preparation of 95% to 99% or more homogeneity most preferred, particularly for pharmaceutical uses.

Kunitz-type inhibitor activity may be measured using the method essentially described by Norris et al. (*Biol. Chem. Hoppe-Seyler* 371: 37–42, 1990). Briefly, various fixed concentrations of the Kunitz-type inhibitor are incubated in the presence of 0.24 µg/ml of porcine. trypsin (Novo Nordisk A/S, Bagsvaerd, Denmark), 12.8 CU/l human plasmin (Kabi, Stockholm, Sweden) or 0.16 nkat/ml human plasma kallikrein (Kabi) in 100 mM NaCl, 50 mM Tris HCl, 0.01% TWEEN 80 (Polyoxyethylenesorbitan monoleate) (pH 7.4) at 25° C. After a 30 minute incubation, the residual enzymatic activity is measured by the cleavage of a solution containing 0.6 mM of either of the chromogenic peptidyl nitroanilide trypsin/plasmin substrates S2251 (D-Val-Leu-Lys-Nan; Kabi) or S2302 (D-Pro-Phe-Arg-Nan; Kabi) in assay buffer. The samples are incubated for 30 minutes after which the absorbance of each sample is measured at 405 nm. An inhibition of enzyme activity is measured as a decrease in absorbance at 405 nm or fluorescence Em at 460 nm. From the results, the apparent inhibition constant $K_i$ is calculated.

The Kunitz-type inhibitors of the present invention may be used in the disclosed methods for the treatment of, *inter alia*, deep vein thrombosis, disseminated intravascular coagulation, pulmonary embolism and for the prevention of thrombosis following surgery.

The present invention relates to novel human Kunitz-type inhibitors comprising the amino acid sequence shown in SEQ ID NO:15, SEQ ID NO:2 or portions thereof and/or encoded by a DNA sequence comprising the nucleotide sequence of SEQ ID NO:14, SEQ ID NO:1 or portions thereof. A comparison of the amino acid sequence SEQ ID NO:2 of TFPI-2 with other Kunitz-type inhibitors, more particularly with TFPI, showed that the protein contains three putative Kunitz-type inhibitor domains. As will be evident to one skilled in the art, each individual domain or combinations of the domains may be prepared synthetically or by recombinant DNA techniques for use in the present invention. The putative Kunitz-type inhibitor domains comprise the amino acid sequence shown SEQ ID NO:2 from cysteine, amino acid number 36 through cysteine, amino acid number 86; from cysteine, amino acid number 96 through cysteine, amino acid number 149; and from cysteine, amino acid 158 through cysteine amino acid 208. More particularly, the Kunitz-type inhibitors of the present invention comprise the amino acid sequence of SEQ ID NO:2 from cysteine, amino acid number 36 through cysteine, amino acid number 86. Kunitz domains are defined by the location of the six specifically placed cysteine residues which are believed to form disulfide bonds (See Laskowski and Kato, ibid. and Broze et al., *Biochemistry* 29: 7539–7546, 1990). The first and sixth cysteine residues define the boundaries of each Kunitz domain. Thus, in the case of TFPI-2, the Kunitz domains are bounded by residues 36 and 86, 96 and 149, 158 and 208 (numbered in accordance with SEQ ID NO:2). To provide the proper disulfide bond formation and protein conformation it is desirable to include at least two amino acid residues flanking each of the cysteine residues defining the Kunitz domain. However, the identities of these flanking residues are not critical. It is thus possible to prepare variants of the individual Kunitz domains comprising the "core" Kunitz sequences described above, wherein the polypeptide core is flanked on its amino and carboxyl termini by from two to four or more amino acid residues other than cysteine residues. Furthermore, as will be evident to one skilled in the art, amino-terminal and/or carboxyl-terminal extensions of the Kunitz-type inhibitor may be prepared either synthetically or using recombinant DNA techniques and tested for inhibitor activity.

The DNA sequences encoding the proteins of the present invention were unexpectedly identified during screening for a cDNA corresponding to the genomic clone of a related but distinct Kunitz-type inhibitor using an antisense oligonucleotide probe complementary to a portion of the inhibitor coding sequence. Analysis of the cDNA clones revealed clones that encoded a unique, previously unknown Kunitz-type inhibitor, designated TFPI-2. The proteins of the present invention may be encoded by DNA sequences that are substantially similar to the DNA sequence disclosed herein. As used within the context of the present invention, "substantially similar" DNA sequences encompass allelic variants and genetically engineered or synthetic variants of the TFPI-2 gene that contain conservative amino acid substitutions and/or minor additions, substitutions or deletions of amino acids. DNA sequence variants also encompass degeneracies in the DNA code wherein host-preferred codons are substituted for the analogous codons in the human sequence. In addition, substantially similar DNA sequences are those that are capable of hybridizing to the DNA sequences of the present invention under high or low stringency (see Sambrook et al., ibid.) and those sequences that are degenerate as a result of the genetic code, for example, to the amino acid sequences of the present invention. Genetically engineered variants may be obtained by using oligonucleotide-directed site-specific mutagenesis, by use of restriction endonuclease digestion and adapter ligation, or other methods well established in the literature (see for example, Sambrook et al., ibid. and Smith et al., *Genetic Engineering: Principles and Methods*, Plenum Press, 1981; which are incorporated herein by reference).

DNA molecules of the present invention may be isolated using standard cloning methods such as those described by Maniatis et al. (*Molecular Cloning: A Laboratory Manual*, Cold Spring Harbor, N.Y., 1982; which is incorporated herein by reference), Sambrook et al. (*Molecular Cloning: A Laboratory Manual, Second Edition*, Cold Spring Harbor, N.Y., 1989; which is incorporated herein by reference) or Mullis et al. (U.S. Pat. No. 4,683,195; incorporated herein by reference). Alternatively, the coding sequences of the present invention may be synthesized using standard techniques that are well known in the art, such as by synthesis on an automated DNA synthesizer. As will be discussed in more detail below, a novel, previously unknown human Kunitz-type inhibitor was identified as a 1.0 kb cDNA insert and comprises the DNA sequence of SEQ ID NO:1. In one embodiment of the invention, DNA sequences encoding the Kunitz-type inhibitors of the present invention are obtained by PCR amplification using primers designed from SEQ ID NO:1 or its complement.

DNA molecules encoding TFPI-2 may also be obtained from non-human animals such as dogs, rabbits, chicken, pigs, mice, rats and cows by screening placental, liver or umbilical vein cell cDNA or genomic libraries using the DNA sequences and methods disclosed herein.

DNA molecules of the present invention or portions thereof may be used as probes, for example, to directly detect TFPI-2 sequences in cells. Such DNA molecules are generally synthetic oligonucleotides, but may be generated from cloned cDNA or genomic sequences and will generally comprise at least 12 nucleotides, more often from about 14 nucleotides to about 25 or more nucleotides, sometimes 40 to 60 nucleotides, and in some instances a substantial portion or even the entire TFPI-2 gene or cDNA. The synthetic oligonucleotides of the present invention have at least 85% identity to a corresponding TFPI-2 DNA sequence (SEQ ID NO:1) or its complement. For use as probes, the molecules are labeled to provide a detectable signal, such as with an enzyme, biotin, a radionuclide, fluorophore, chemiluminescer, paramagnetic particle, etc. according to methods known in the art. Probes of the present invention may be used, diagnostic methods to detect cellular metabolic disorders such as thrombolic disorders.

DNA molecules used within the present invention may be labeled and used in a hybridization procedure similar to the Southern or dot blot. As will be understood by those skilled in the art, conditions that allow the DNA molecules of the present invention to hybridize to the TFPI-2 sequences may be determined by methods well known in the art and are reviewed, for example, by Sambrook et al. (*Molecular Cloning: A Laboratory Manual, Second Edition*, Cold Spring Harbor, N.Y., 1989; which is incorporated herein by reference). Those skilled in the art will be capable of varying hybridization conditions (i.e. stringency of hybridization) of the DNA molecules as appropriate for use in the various procedures by methods well known in the literature (see, for example, Sambrook et al., ibid., pages 11.45–11.53). The higher the stringency of hybridization, the lower the number of mismatched sequences detected. Alternatively, lower stringency will allow related sequences to be identified.

Alternatively, TFPI-2 protein sequence variants may be identified using DNA molecules of the present invention and, for example, the polymerase chain reaction (PCR) (disclosed by Saiki et al., *Science* 239: 487, 1987; Mullis et al., U.S. Pat. No. 4,686,195; and Mullis et al., U.S. Pat. No. 4,683,202) to amplify DNA sequences, which are subsequently detected by their characteristic size on agarose gels or which may be sequenced to detect sequence abnormalities.

DNA molecules encoding the Kunitz-type inhibitors of the present invention may be inserted into DNA constructs. As used within the context of the present invention, a DNA construct, also known as an expression vector, is understood to refer to a DNA molecule, or a clone of such a molecule, either single-or double-stranded, which has been modified through human intervention to contain segments of DNA combined and juxtaposed in a manner that would not otherwise exist in nature. DNA constructs of the present invention comprise a first DNA segment encoding a Kunitz-type inhibitor operably linked to additional DNA segments required for the expression of the first DNA segment. Within the context of the present invention, additional DNA segments will generally include promoters and transcription terminators, and may further include enhancers and other elements. One or more selectable markers may also be included. DNA constructs useful for expressing cloned DNA segments in a variety of prokaryotic and eukaryotic host cells can be prepared from readily available components or purchase from commercial suppliers.

In one embodiment the DNA sequence encodes a Kunitz-type inhibitor comprising the amino acid sequence of SEQ ID NO:15 wherein each Xaa is individually any amino acid except cysteine. In another embodiment the DNA sequence encodes a Kunitz-type inhibitor comprising the amino acid sequence of SEQ ID NO:2 from methionine, amino acid number 1 through phenylalanine, amino acid number 235. In another embodiment, the first DNA sequence encodes a Kunitz-type inhibitor comprising the amino acid sequence of SEQ ID NO:2 from glutamic acid, amino acid 34 to isoleucine, amino acid number 89. In another embodiment of the invention, the Kunitz-type inhibitor comprises the amino acid sequence of SEQ ID NO:2 from glutamic acid, amino acid number 34 to lysine, amino acid number 152. In yet another embodiment of the invention, the Kunitz-type inhibitor comprises the amino acid sequence of SEQ ID NO:2 from glutamic acid, amino acid number 34 to alanine, amino acid number 211.

DNA constructs may also contain DNA segments necessary to direct the secretion of a polypeptide or protein of interest. Such DNA segments may include at least one secretory signal sequence. Secretory signal sequences, also called leader sequences, prepro sequences and/or pre sequences, are amino acid sequences that act to direct the secretion of mature polypeptides or proteins from a cell. Such sequences are characterized by a core of hydrophobic amino acids and are typically (but not exclusively) found at the amino termini of newly synthesized proteins. Very often the secretory peptide is cleaved from the mature protein during secretion. Such secretory peptides contain processing sites that allow cleavage of the secretory peptide from the mature protein as it passes through the secretory pathway. A preferred processing site is a dibasic cleavage site, such as that recognized by the *Saccharomyces cerevisiae* KEX2 gene. A particularly preferred processing site is a Lys-Arg processing site. Processing sites may be encoded within the secretory peptide or may be added to the peptide by, for example, in vitro mutagenesis.

Preferred secretory signals include the α factor signal sequence (prepro sequence: Kurjan and Herskowitz, *Cell* 30: 933–943, 1982; Kurjan et al., U.S. Pat. No. 4,546,082; Brake, EP 116,201), the PHO5 signal sequence (Beck et al., WO 86/00637), the BAR1 secretory signal sequence (MacKay et al., U.S. Pat. No. 4,613,572; MacKay, WO 87/002670), the SUC2 signal sequence (carlsen et al., *Molecular and Cellular Biology* 3: 439–447, 1983), the α-1-antitrypsin signal sequence (Kurachi et al., *Proc. Natl. Acad. Sci. USA* 78: 6826–6830, 1981) the α-2 plasmin inhibitor signal sequence (Tone et al., *J. Biochem.* (Tokyo) 102: 1033–1042, 1987) and the tissue plasminogen activator signal sequence (Pennica et al., *Nature* 301: 214–221, 1983). Alternately, a secretory signal sequence may be synthesized according to the rules established, for example, by yon Heinje (*European Journal of Biochemistry* 133: 17–21, 1983; *Journal of Molecular Biology* 184: 99–105, 1985; *Nucleic Acids Research* 14: 4683–4690, 1986). A particularly preferred signal sequence is the synthetic signal LaC212 spx (1–47)—ERLE described in WO 90/10075, which is incorporated by reference herein in its entirety.

Secretory signal sequences may be used singly or may be combined. For example, a first secretory signal sequence may be used in combination with a sequence encoding the third domain of barrier (described in U.S. Pat. No. 5,037,243, which is incorporated by reference herein in its entirety). The third domain of barrier may be positioned in proper reading frame 3' of the DNA segment of interest or 5' to the DNA segment and in proper reading frame with both the secretory signal sequence and a DNA segment of interest.

The choice of suitable promoters, terminators and secretory signals is well within the level of ordinary skill in the art. Methods for expressing cloned genes in *Saccharomyces cerevisiae* are generally known in the art (see, , "Gene Expression Technology," *Methods in Enzymology*, Vol. 185, Goeddel (ed.), Academic Press, San Diego, Calif., 1990 and "Guide to Yeast Genetics and Molecular Biology," *Methods in Enzymology*, Guthrie and Fink (eds.), Academic Press, San Diego, Calif., 1991; which are incorporated herein by reference). Proteins of the present invention can also be expressed in filamentous fungi, for example, strains of the fungi *Aspergillus* (McKnight et al., U.S. Pat. No. 4,935,349, which is incorporated herein by reference). Expression of cloned genes in cultured mammalian cells and in *E. coli*, for example, is discussed in detail in Sambrook et al. (*Molecular Cloning: A Laboratory Manual, Second Edition*, Cold Spring Harbor, N.Y., 1989; which is incorporated herein by reference). As would be evident to one skilled in the art, one could express the proteins of the instant invention in other host cells such as avian, insect and plant cells using regulatory sequences, vectors and methods well established in the literature.

In yeast, suitable yeast vectors for use in the present invention include YRp7 (Struhl et al., *Proc. Natl. Acad. Sci. USA* 76: 1035–1039, 1978), YEp13 (Broach et al., *Gene* 8: 121–133, 1979), POT vectors (Kawasaki et al, U.S. Pat. No. 4,931,373, which is incorporated by reference herein), pJDB249 and pJDB219 (Beggs, *Nature* 275:104–108, 1978) and derivatives thereof. Preferred promoters for use in yeast include promoters from yeast glycolytic genes (Hitzeman et al., *J. Biol. Chem.* 255: 12073–12080, 1980; Alber and Kawasaki, *J. Mol. Appl. Genet.* 1: 419–434, 1982; Kawasaki, U.S. Pat. No. 4,599,311) or alcohol dehydrogenase genes (Young et al., in *Genetic Engineering of Microorganisms for Chemicals*, Hollaender et al., (eds.), p. 355, Plenum, New York, 1982; Ammerer, *Meth. Enzymol.* 101: 192–201, 1983). In this regard, particularly preferred promoters are the TPI1 promoter (Kawasaki, U.S. Pat. No. 4,599,311, 1986) and the ADH2-4$^c$ promoter (Russell et al., *Nature* 304: 652–654, 1983; irani and Kilgore, U.S. patent application Ser. No. 07/784,653, CA 1,304,020 and EP 284 044, which are incorporated herein by reference). The expression units may also include a transcriptional terminator. A preferred transcriptional terminator is the TPI1 terminator (Alber and Kawasaki, ibid.).

Host cells containing DNA constructs of the present invention are then cultured to produce the Kunitz-type inhibitors. The cells are cultured according to standard methods in a culture medium containing nutrients required for growth of the particular host cells. A variety of suitable media are known in the art and generally include a carbon source, a nitrogen source, essential amino acids, vitamins, minerals and growth factors. The growth medium will generally select for cells containing the DNA construct by, for example, drug selection or deficiency in an essential nutrient which is complemented by a selectable marker on the DNA construct or co-transfected with the DNA construct.

Yeast cells, for example, are preferably cultured in a chemically defined medium, comprising a non-amino acid nitrogen source, inorganic salts, vitamins and essential amino acid supplements. The pH of the medium is preferably maintained at a pH greater than 2 and less than 8, preferably at pH 6.5. Methods for maintaining a stable pH include buffering and constant pH control, preferably through the addition of sodium hydroxide. Preferred buffering agents include succinic acid and Bis-Tris (Sigma Chemical Co., St. Louis, Mo.). Yeast cells having a defect in a gene required for asparagine-linked glycosylation are preferably grown in a medium containing an osmotic stabilizer. A preferred osmotic stabilizer is sorbitol supplemented into the medium at a concentration between 0.1M and 1.5M, preferably at 0.5M or 1.0M. Cultured mammalian cells are generally cultured in commercially available serum-containing or serum-free media. Selection of a medium appropriate for the particular host cell used is within the level of ordinary skill in the art.

Within one embodiment of the invention, the proteins of the present invention are expressed in mammalian cells. Methods for introducing exogenous DNA into mammalian host cells include calcium phosphate-mediated transfection (Wigler et al., *Cell* 14:725, 1978; Corsaro and Pearson, *Somatic Cell Genetics* :7:603, 1981: Graham and Van der Eb, *Virology* 52:456, 1973), electroporation (Neumann et al., *EMBO J.* 1:841–845, 1982) and DEAE-dextran mediated transfection (Ausubel et al., eds., *Current Protocols in Molecular Biology*, John Wiley and Sons, Inc., N.Y., 1987), which are incorporated herein by reference.. Cationic lipid transfection using commerically available reagents including the Boehringer Mannheim Transfection-Reagent (N-[1-(2,3-Dioleoyloxy)propyl]-N,N,N-trimethyl ammoniummethylsulfate; Boehringer Mannheim, Indianapolis, IN) or LIPOFECTIN reagent (N-[1-(2,3-dioleyloxy)propyl]-N,N, N-trimethylammonium chloride and dioeleoyl phosphatidylethanolamine; GIBCO-BRL, Gaithersburg, Md.) using the manufacturer-supplied directions, may also be used. The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314) and 293 (ATCC No. CRL 1573; Graham et al., *J. Gen. Virol.* 36:59–72, 1977) cell lines. Additional suitable cell lines are known in the art and available from public depositories such as the American Type Culture Collection, Rockville, Md.

The recombinant Kunitz-type inhibitors expressed using the methods described herein are isolated and purified by conventional procedures, including separating the cells from the medium by centrifugation or filtration, precipitating the proteinaceous components of the supernatant or filtrate by means of a salt, e.g. ammonium sulfate, purification by a variety of chromatographic procedures, e.g. ion exchange chromatography or affinity chromatography, or the like. Methods of protein purification are known in the art (see generally, Scopes, R., *Protein Purification*, Springer-Verlag, N.Y. (1982), which is incorporated herein by reference) and may be applied to the purification of the recombinant proteins of the present invention.

The Kunitz-type inhibitors of the present invention may be purified using the ability of the inhibitor to bind to trypsin. Briefly, a total of approximately 1 liter fermentation supernatant is adjusted to pH 8.0 by the addition of solid Tris-HCl to a final concentration of 50 mM and titration with 4M NaOH. After filtration to remove any cellular debris, the supernatant is applied to a column of bovine trypsin adsorbed to CNBr-activated Sepharose (350 mg bovine trypsin per 35 ml gel). The column is washed sequentially with 150 ml 0.1M Tris-HCl (pH 8.0), 0.5M NaCl , then 150 ml 0.01M Tris-HCl (pH 8.0) before the bound material is eluted with 200 ml 0.2M glycine-HCl (pH 3.0). Fractions of 10 ml are collected and analyzed by reverse phase HPLC. Protein-containing fractions are combined.

The pooled material is applied to a preparative reverse phase HPLC column, (Vydac, The Separations Group, Hesperia, Calif. or the like) equilibrated with 5% B (0.7% TFA in acetonitrile) and 95% A (0.1% TFA in $H_2O$). The flow rate is maintained at 4 ml/min. Following application of sample, the column is washed with 5% B until a baseline at 214 nm is achieved. Gradient elution with fraction collection is performed from 5 to 85% B over 80 min. Fractions containing UV-absorbing material are analyzed by reverse phase HPLC (Vydac) and combined to give pools of chromatographically pure material. Solvent is removed from the pooled fractions by vacuum centrifugation. The concentration and total yield of inhibitor in the major pools is estimated by reverse phase HPLC analysis and by comparison to an aprotinin standard. The final preparations are characterized by electrospray mass spectroscopy (SCIEX API III) or the like.

In cases where proteolytic cleavage of the Kunitz inhibitor is a potential problem, the Kunitz inhibitors of the present invention may also be purified using the method essentially described by Norris et al. (*Biol. Chem. Hoppe-Seyler* 371: 37–42, 1990, which is incorporated by reference herein in its entirety). Briefly, selected transformants are grown in 10 liters of YEPD for approximately 40 hours at 30° C. until an $OD_{600}$ of approximately 25 has been reached. The culture is centrifuged, and the supernatant is decanted. A 300 ml-1000 ml aliquot of supernatant is adjusted to pH 2.3 and applied to a column holding 8 ml of beaded agarose matrix such as S-Sepharaose (Pharmacia-LKB Biotechnology AS, Alleroed, Denmark) or the like that has been previously equilibrated with 20 mM Bicine, pH 8.7 (Sigma Chemical Co., St. Louis, Mo.). After the column has been extensively washed with 20 mM Bicine, pH 8.7, the Kunitz-type inhibitor is eluted with 30 ml of 20 mM Bicine, pH 8.7 containing 1M NaCl. The eluted material is desalted by application to a Sephadex G-25 column (a beaded dextran matrix, Pharmacia-LKB Biotechnology AS, Alleroed, Denmark; 2.5×30 cm) or the like that has been equilibrated with 20 mM $NH_4HCO_3$, pH 7.8. The Kunitz-type inhibitor is eluted with 20 mM $NH_4HCO_3$, pH 7.8.

The Kunitz-type inhibitors are further purified and concentrated by chromatography on a column containing a cation exchanger with charged sulfonic groups coupled to a beaded hydrophylic resin such as a MONO S column (Pharmacia-LKB Biotechnology AS, Alleroed, Denmark; 0.5×5 cm) or the like equilibrated with 20 mM Bicine, pH 8.7. After washing with the equilibration buffer at 2 ml/min for 10 minutes, gradient elution of the Kunitz-type inhibitor is carried out over twelve minutes at 1 ml/min from 0–0.6M NaCl in the equilibration buffer. Peak samples are pooled, and the Kunitz-type inhibitor is purified using reverse phase HPLC on a Vydac 214TP510 column (Mikro-lab, Aarhus, Denmark; 1.0×25 cm) or the like with a gradient elution at 4 ml/min from 5% A (0.1% trifluoroacetic acid (TFA) in water) to 45% B (0.7% TFA in acetonitrile) in 20 minutes. The purified product in lyophilized in water, and inhibitor activity is measured.

Alternatively, TFPI-2 may be purified from conditioned medium by sequential chromatography using heparin agarose, an anion exchanger with quaternary amine groups crosslinked to a beaded hydrophylic resin such as MONO Q (Pharmacia) or the like, a cation exchanger with charged sulfonic groups coupled to a beaded hydrophylic resin such as MONO S (Pharmacia) or the like and cross-linked agarose gel filtration matrix having different porosities for the separation of proteins from $1\times10^3$ to $3\times10^5$ MW such as SUPEROSE 12 (Pharmacia) or the like. Briefly, conditioned serum-free media, adjusted to pH 7.5 with 1N NaOH and filtered through a 0.22-μm filter, is applied to a heparin sepharose column (Pharmacia Biotech Inc., Piscataway, N.J.) or the like that has been equilibrated at 4° C. with Buffer A (50 mM Tris-HCl (pH 7.5), 10% glycerol). The filtered media is applied at a flow rate of 3 ml/min. The column is washed with Buffer A containing 0.2M NaCl. TFPI-2 activity, as judged by its ability to inhibit trypsin (Example 4A), is eluted from the column with Buffer A containing 1M NaCl. The eluent from the heparin sepharose column is dialyzed at 4° C. against 25 mM Tris-HCl (pH 7.5), 10% glycerol. The retentate is subjected to FPLC (Pharmacia Biotech Inc.) on a 5×50 mm column containing an anion exchanger with quaternary amine groups crosslinked to a beaded hydrophylic resin such as a MONO Q (MONO Q HR 5/5; Pharmacia Biotech Inc., Piscataway, N.J.) or the like that had been equilibrated with 25 mM Tris-HCl (pH 7.5), 10% glycerol at room temperature. TFPI-2 is eluted from the column in a linear NaCl gradient (from 0–0.5M NaCl) at a flow rate of 1 ml/min. The TFPI-2 fractions are pooled and dialyzed against 25 mM sodium citrate (pH 5.0), 10% glycerol. The retentate is then subjected to FPLC at room temperature on a cation exchanger with charged sulfonic groups coupled to a beaded hydrophylic resin such as MONO S (MONO S HR 5/5, Pharmacia Biotech Inc.) or the like at a flow rate of 0.5 ml/min. TFPI-2 activity is eluted from the MONO S column with a gradient elution from 25 mM sodium citrate (pH 5.0), 10% glycerol to 25 mM Tris-HCl (pH 7.5), 10% glycerol, 1M NaCl. Fractions containing TFPI-2 activity are pooled and concentrated to approximately 1 ml by ultrafiltration. The concentrated samples are subjected to FPLC across a crosslinked agarose gel filtration matrix having a porosity suitable for the separation of proteins from $1\times10^3$ to $3\times10^5$ MW such as SUPEROSE 12 (Pharmacia Biotech Inc., Piscataway, N.J.) or the like at room temperature in 50 mM Tris-HCl (pH 7.5), 100 mM NaCl. Fractions eluted from the FPLC with TFPI-2 activity were subjected to SDS-PAGE, and pure fractions are pooled and stored at −80° C.

The present invention also relates to a pharmaceutical composition comprising a Kunitz-type inhibitor of the present invention together with a pharmaceutically acceptable carrier or vehicle. In the composition of the invention, the Kunitz-type inhibitor may be formulated by any of the established methods of formulating pharmaceutical compositions, e.g. as described in *Remington's Pharmaceutical Sciences*, 1985. The composition may typically be in a form suited for systemic injection or infusion and may, as such, be formulated with sterile water or an isotonic saline or glucose solution.

Kunitz-type inhibitors of the present invention are therefore contemplated to be advantageous for use in therapeutic applications for which tissue factor pathway inhibitor are useful. Such applications include disseminated intravascular coagulation, deep vein thrombosis, pulmonary embolism and in the prevention of thrombosis following surgery. As will be evident to one skilled in the art, the Kunitz-type inhibitors of the present invention may be combined with other therapeutic agents to augment the antithrombotic or anticoagulant activity of such agents. TFPI-2 may, for example, be used in conjunction with tissue plasminogen activator in thrombolytic therapy. The use of the Kunitz-type inhibitors of the present invention is indicated as a result of their ability to inhibit factor VIIa/tissue factor complex.

Thus, the Kunitz-type inhibitors of the present invention may be used within methods for inhibiting blood coagulation in mammals. Such methods will generally include administering the Kunitz-type inhibitor in an amount sufficient to inhibit blood coagulation. Such amounts can vary according to the severity of the condition being treated and may range from approximately 10 µg/kg to 10 mg/kg body weight. Preferably the amount of the Kunitz-type inhibitor administered will be within the range of 100 µg/kg and 5 mg/kg with a range of 100 µg/kg and 1 mg/kg as the most preferable range.

Apart from the pharmaceutical use indicated above, the Kunitz-type inhibitors as specified above may be used to isolate useful natural substances, e.g. proteases or receptors from human material, which bind directly or indirectly to the Kunitz-type inhibitor, for instance by screening assays or by affinity chromatography.

Within one aspect of the present invention, Kunitz-type inhibitors, including derivatives thereof, as well as portions or fragments of these proteins, are utilized to prepare antibodies which specifically bind to the Kunitz-type inhibitors. As used herein, the term "antibodies" includes polyclonal antibodies, monoclonal antibodies, antigen-binding fragments thereof such as $F(ab')_2$ and Fab fragments, as well as recombinantly produced binding partners. These binding partners incorporate the variable regions from a gene which encodes a specifically binding monoclonal antibody. Antibodies are defined to be specifically binding if they bind to the Kunitz-type inhibitor with a $K_a$ of greater than or equal to $10^7$/M. The affinity of a monoclonal antibody or binding partner may be readily determined by one of ordinary skill in the art (see, Scatchard, Ann. NY Acad. Sci. 51: 660–672, 1949). Isolated antibodies are those antibodies that are substantially free of other blood.

Methods for preparing polyclonal and monoclonal antibodies have been well described in the literature (see for example, Sambrook et al., ibid.; Hurrell, J. G. R., Ed., *Monoclonal Hybridoma Antibodies: Techniques and Applications*, CRE Press, Inc., Boca Raton, Fla., 1982). As would be evident to one of ordinary skill in the art, polyclonal antibodies may be generated from a variety of warm-blooded animals such as horses, cows, goats, sheep, dogs, chickens, rabbits, mice, or rats. The immunogenicity of the Kunitz-type inhibitor may be increased through the use of an adjuvant such as Freund's complete or incomplete adjuvant. A variety of assays known to those skilled in the art may be utilized to detect antibodies which specifically bind to a Kunitz-type inhibitor. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immuno-sorbent assays, dot blot assays, inhibition or competition assays, and sandwich assays.

Additional techniques for the preparation of monoclonal antibodies may utilized to construct and express recombinant monoclonal antibodies. Briefly, mRNA is isolated from a B cell population and utilized to create heavy and light chain immunoglobulin cDNA expression libraries in a suitable vector such as the λ IMMUNOZAP(H) and λIMMUNOZAP(L) vectors, which may be obtained from Stratocyte (La Jolla, Calif.). These vectors are then screened individually or are co-expressed to form Fab fragments or antibodies (Huse et al., *Science* 246: 1275–1281, 1989; Sastry et al., *Proc. Natl. Acad. Sci. USA* 86: 5728–5732, 1989). Positive plaques are subsequently converted to a non-lytic plasmid which allows high level expression of monoclonal antibody fragments in *E. coli*.

Binding partners such as those described above may also be constructed utilizing recombinant DNA techniques to incorporate the variable regions of a gene which encodes a specifically binding antibody. The construction of these proteins may be readily accomplished by one of ordinary skill in the art (see for example, Larrick et al., *Biotechnology* 7: 934–938, 1989; Reichmann et al., *Nature* 322: 323–327, 1988 and Roberts et al. *Nature* 328: 731–734, 1987). Once suitable antibodies or binding partners have been obtained, they may be isolated or purified by many techniques well described in the literature (see for example, *Antibodies: A Laboratory Manual*, ibid.). Suitable techniques include protein or peptide affinity columns, HPLC or RP-HPLC, purification on protein A or protein G columns or any combination of these techniques. Within the context of the present invention, the term "isolated" as used to define antibodies or binding partners means "substantially free of other blood components."

Antibodies and binding partners of the present invention may be used in a variety of ways. The tissue distribution of the Kunitz-type inhibitor, for example, may be determined by incubating tissue slices with a labeled monoclonal antibody which specifically binds to the Kunitz-type inhibitor, followed by detection of the presence of the bound antibody. Labels suitable for use within the present invention are well known in the art and include, among others, fluorescein, isothiocyanate, phycoerythrin, horseradish peroxidase, and colloidal gold. The antibodies of the present invention may also be used for the purification of the Kunitz-type inhibitors of the present invention. The coupling of antibodies to solid supports and their use in purification of proteins is well known in the literature (see for example, *Methods in Molecular Biology*, Vol. 1, Walker (Ed.), Humana Press, New Jersey, 1984, which is incorporated by reference herein in its entirety).

The following examples are offered by way of illustration, not by way of limitation.

EXAMPLES

Restriction endonucleases and other DNA modification enzymes (e.g., T4 polynucleotide kinase, calf alkaline phosphatase, DNA polymerase I (Klenow fragment), T4 polynucleotide ligase) were obtained from GIBCO BRL Life Technologies, Inc (GIBCO BRL) and New England Biolabs and were used as directed by the manufacturer, unless otherwise noted.

Oligonucleotides were synthesized on an Applied Biosystems Model 380A DNA synthesizer and purified by polyacrylamide gel electrophoresis on denaturing gels. *E. coli* cells were transformed as described by Maniatis et al. (*Molecular Cloning: A Laboratory Manual*, Cold Spring Harbor Laboratory, 1982) or Sambrook et al. (*Molecular Cloning: A Laboratory Manual*, 2 ed., Cold Spring Harbor, N.Y., 1989). Radiolabeled probes and hybridization solutions were prepared essentially as described by Sambrook et al. (*Molecular cloning: A Laboratory Manual*, 2 ed., Cold Spring Harbor, N.Y., 1989; which is incorporated by reference herein in its entirety).

EXAMPLE 1

Cloning of A Novel Human Kunitz Inhibitor cDNA

Poly(A)⁺RNAs from a variety of human tissue sources were screened using an antisense 30-meroligonucleotide (ZC4792; SEQ ID NO:3). A blot of human Poly(A)⁺RNA from heart, brain, placenta, liver, lung, skeletal muscle, kidney and pancreas (HUMAN MTN BLOT) was obtained from Clontech Laboratories, Inc. (Palo Alto, Calif.). The blot was prehybridized in a Prehybridization solution (5× SSPE (Table 1), 2× Denhardt's (Table 1), 0.5% sodium dodecyl-sulfate (SDS), 100 µg/ml of sonicated salmon sperm DNA) for four hours at 55° C. After prehybridization, the prehybridization solution was removed and replaced with prehybridization solution containing $4.7 \times 10^6$ cpm/ml of $^{32}$P-labeled ZC4792 (SEQ ID NO:3). After an overnight incubation at 55° C. the hybridization solution was removed, and the blot was washed once in 2× SSC (Table 1), 0.05% SDS at room temperature for 20 minutes followed by a wash in 2× SSC (Table 1), 0.1% SDS for 20 minutes at 55° C. The blot was exposed to film for two and a half hours. The resulting autoradiograph showed a number of bands in most of the lanes, indicating the presence of related sequences in most of the tissues represented in the blot. The blot was washed at a higher stringency in 2× SSC (Table 1) at a temperature between 60° C. and 65° C. for 30 minutes, after which the blot was exposed to film overnight. The second autoradiograph showed the presence of a 1.6 kb band for placenta and liver and an apparently smaller band of approximately 1.2 kb in the pancreas.

TABLE 1

20× SSPE 175.3 g NaCl
27.6 g NaH$_2$PO$_4$.H$_2$O
7.4 g EDTA
Dissolve the solids in 800 ml of distilled water. Adjust the pH to 7.4 with NaOH (approximately 6.5 ml of a 10 N solution). Adjust the volume to 1 liter with distilled water. Sterilize by autoclaving.
50× Denhardt's 5 g Ficoll
5 g polyvinylpyrrolidone
5 g bovine serum albumin (Fraction V)
Dissolve the solids into a final volume of 500 ml. Filter the solution to sterilize and store at −20° C.
20× SSC 175.3 g NaCl
88.2 g sodium citrate
Dissolve the solids in 800 ml of distilled water. Adjust the pH to 7.0 by a drop-wise addition of 10 N NaOH. Adjust the volume to 1 liter with distilled water. Sterilize by autoclaving.
Prehybridization Solution #1

5× SSPE
5× Denhardt's
0.5% SDS
100 µg/ml sheared salmon sperm DNA
Prehybridization Solution #2

5× SSC
5× Denhardt's
0.1% SDS
100 µg/ml sheared salmon sperm DNA
Growth Medium

Dulbecco's Modified Eagle's Medium (DMEM) containing 5% fetal bovine serum, 2 mM L-glutamate, 1× PSN (50 µg/ml penicillin, 50 µg/ml streptomycin, 100 µg/ml neomycin; GIBCO BRL), 10 µM methotrexate.
Serum-free Medium 500 ml Dulbecco's Modified Eagle's Medium (DMEM)
0.29 mg/ml L-glutamine
10 mg/L transferrin
5 mg/L fetuin (Aldrich, Milwaukee, WI)

TABLE 1-continued 5 mg/L insulin (GIBCO BRL, Grand Island, NY)
2 µg/L selenium (Aldrich, Milwaukee, WI)
In addition to the above ingredients, the medium was supplemented with 10 µM methotrexate, 25–50 mM HEPES BUFFER SOLUTION (N-2-Hydroxyethylpiperazine-N'-2-Ethane Sulfonic Acid (pH 7.2); JRH Biosciences, Lenxa, KS) and 1× PSN (GIBCO BRL).
Phosphate Buffered Saline (PBS)

8 g sodium chloride
0.2 g potassium chloride
1 g sodium phosphate
2 g potassium phosphate
Dissolve solids in distilled water. Bring volume to 1 liter. Autoclave to sterilize.

To obtain a cDNA encoding a human placental protease inhibitor from the Kunitz family, a human placenta cDNA library in λgt11 (Clontech Laboratories, Inc., Palo Alto, Calif.) was screened using the radio-labeled ZC4792 (SEQ ID NO:3) essentially as described above. The library was titered, and $2 \times 10^5$ pfu/plate were plated on a total of twelve plates to obtain 2.4 million independent plaques. Duplicate plaque lifts were prepared using ICN BIOTRANS nylon membranes (ICN, Irvine, Calif.). The membranes were prewashed in 5× SSC (Table 1), 0.5% SDS at 50° C. for one hour followed by an overnight prehybridization at 55° C. in prehybridization solution #1 (Table 1). The prehybridization solution was removed and replaced with fresh prehybridization solution #1 (Table 1) containing $7.2 \times 10^7$ cpm of ZC4792 probe (SEQ ID NO:3). Hybridization was carried out under the same conditions as the prehybridization. The hybridization solution was removed, and the blots were washed at 60° C. in 2× SSC (Table 1), 0.1% SDS. Fourteen positive plaques were identified and plaque purified using radio-labeled ZC4792 (SEQ ID NO:3).

Tertiary filters from the plaque purifications of the fourteen clones were probed with a specific fragment from ZGKI13, a clone containing the amyloid precursor protein homologue coding sequence (deposited with the American Type Culture Collection, 12301 ParkLawn Dr., Rockville, Md. on Oct. 14, 1992, as an *E. coli* transformant under accession number ATCC 69090) to identify and eliminate clones having homology with the amyloid precursor protein homologue. A random-primed 880 bp Pst I-Xho I fragment of ZGKI13 was used as a probe. The filters were hybridized overnight at 65° C. in prehybridization solution #2 containing $2 \times 10^6$ cpm/ml of the labeled probe. After hybridization, the solution was removed, and the filters were washed at 65° C. in 0.2× SSC (Table 1), 0.1% SDS. Four of the fourteen plaques were shown to encode the ZGKI13 amyloid protein precursor. These four clones were discarded.

Double-stranded DNA was prepared from one of the ten remaining purified phage clones, designated J-2-11. The plasmid DNA was digested with Eco RI to isolate the approximately 1 kb cDNA insert. The Eco RI fragment was subcloned into Eco RI-linearized pUC19. Sequence analysis of the cloned fragment demonstrated three regions of the clone that showed strong homology to the Kunitz family of protease inhibitors. The tertiary filters of the nine remaining phage clones (described above) were screened determined with a labeled probe specific to the J-2-11 clone. The tertiary filters were hybridized overnight at 55° C. in prehybridization solution #2 (Table 1) containing $2 \times 10^6$ cpm/ml of the kinased oligonucleotide ZC6281 probe (SEQ ID NO:4). After hybridization, the probe was removed, and the filters were washed at 60° C. in 2× SSC (Table 1), 0.1% SDS. Autoradiography of the filters showed that all nine candidate clones contained sequences homologous to J-2-11. One clone was selected and designated J-2-11/pUC19.

Plasmid J-2-11/pUC19 was deposited as an *E. coli* transformant on Sep. 17, 1993 with the American Type Culture Collection (12301 Parklawn Dr., Rockville, Md.) under accession number 69425. Plasmid J-2-11/pUC19 was shown to contain the sequence shown in SEQ ID NO:1. Analysis of the sequence showed a 5' noncoding region of 36 nucleotides, an open reading frame of 705 nucleotides encoding 235 amino acids, and a 235 nucleotide 3' noncoding region. A comparison of the deduced amino acid sequence ((SEQ ID NO:1 and SEQ ID NO:2)with other Kunitz-type type inhibitors showed amino acid homology and domain structure similarities with TFPI.

A blot of poly(A)+mRNA from human tissues (Clontech Multiple Tissue Northern Blot) was screened using a $^{32}$P-end-labeled oligonucleotide corresponding to TFPI-2 sequences (ZC6281; SEQ ID NO:4) to determine the tissue distribution of the transcript. The blot was prehybridized in a prehybridization solution containing 5× SSPE (Table 1), 2× Denhardt's (Table 1), 0.5% SDS, 100 µg/ml salmon sperm DNA at 55° C. for several hours. After prehybridization, the solution was removed, and the blot was hybridized overnight at 55° C. in fresh prehybridization solution containing the kinase ZC6281 (SEQ ID NO:4). The blot was washed at 65° C. in 0.2× SSC (Table 1), 0.1% SDS and exposed to film. Analysis of the autoradiograph indicated that TFPI-2 is transcribed in the placenta and liver. Subsequent northern analysis demonstrated the presence of a TFPI-2 transcript in human umbilical vein endothelial cells One major transcript is apparent at 1.4 kb with a possible minor transcript at ~2 kb. Based on the size of the longest TFPI-2 clones, it is possible that the clone represents an incomplete transcript that is missing some of the 3' noncoding sequence since no polyadenylation sequence is seen. The Eco RI site at the 3' end appears to be an internal site as no linker sequence is seen at this end. Therefore, the mRNA size would predict an additional 400 bp of 3' (or 5') noncoding sequence in a full-length transcript.

EXAMPLE 2

Expression of A Novel Human Kunitz-Type Inhibitor in Cultured Mammalian Cells

The novel human Kunitz-type inhibitor encoded by clone J-2-11 was expressed in the mammalian expression vector Zem229R. The vector Zem229R was deposited on Sep. 28, 1993 with the American Type Culture Collection (12301 Parklawn Dr. Rockville, Md. 20852) as an *E. coli* transformant under accession number 69447. The approximately 1 kb Eco RI fragment from J-2-11/pUC19 was ligated into Zem229R that had been linearized by digestion with Eco RI. Transformants were screened for plasmids containing the insert in the proper orientation relative to the promoter. A positive clone was identified, and plasmid DNA was prepared. The plasmid DNA was used to transfect BHK570 cells using calcium phosphate-mediated transfection (Wigler. et al., *Cell* 14:725, 1978; Corsaro and Pearson, *Somatic Cell Genetics* 7:603, 1981: Graham and Van der Eb, *Virology* 22:456, 1973). BHK 570 cells were deposited with the American Type Culture Collection (ATCC; 12301 Parklawn Dr., Rockville, Md., 20852, U.S.A.) on Dec. 13, 1989 under accession number CRL 10314. Transfected cells were initially selected in the presence of medium containing 1 µM of methotrexate followed by more stringent selection in medium containing 10 µM methotrexate. Following selection in 10 µM methotrexate, randomly selected clones were grown to confluency in 6-well dishes in Growth Medium (Table 1). After reaching confluency, the spent medium was decanted, and the cells were washed with Phosphate Buffered Saline (PBS; Table 1) to remove any remaining serum. Serum-free medium (Table 1) was added to the cells, and the cells were grown for 24–48 hours. The conditioned media was collected and assayed for trypsin inhibitor activity using the assay method detailed in Example 4A.

A clone having the highest level of trypsin inhibitor activity was selected for large-scale culture. Cells from the clone were expanded and seeded into either a small or large cell-factory and were grown to confluency in growth medium (Table 1) containing 10 mg/L aprotinin (Novo Nordisk A/S, Bagsvaerd, Denmark). After reaching confluency, the media was removed, the cells were washed with PBS and serum-free medium (Table 1) containing 10 mg/L aprotinin was added. Media was collected every 2–4 days and stored at –20° C.

EXAMPLE 3

Expression of Kunitz-Type Inhibitor Domains in the Yeast Saccharomyces cerevisiae A. Expression of a Kunitz-type Inhibitor Domain of the TFPI-2 Comprising Amino Acids 34 through 89 of SEQ ID NO:2

The Kunitz-type inhibitor domain encoded in plasmid pJ-2-11/pUC19 and comprising the amino acid sequence of SEQ ID NO:2 from glutamic acid, amino acid 34 through isoleucine, amino acid number 89 is expressed in a strain of the yeast *Saccharomyces cerevisiae* from a PCR-generated sequence. The DNA sequence encoding the Kunitz-type inhibitor domain is amplified from pJ-2-11/pUC19. Synthetic oligonucleotide primers M-2161 and M-2177 (SEQ ID NOS:5 and 6, respectively) are designed as PCR amplification primers. Synthetic oligonucleotide M-2177 is complementary to nucleotides 288–305 of SEQ ID NO:1, and in addition carries a 5' extension containing a translation stop codon followed by an Xba I site. Oligonucleotide M-2161 contains a sequence that is identical to nucleotides 215–235 of the synthetic leader sequence shown in SEQ ID NO:7 followed by nucleotides 138–154 of SEQ ID NO:1. A PCR reaction is performed in a 100 µl final volume using 1 µg plasmid pJ-2-11/pUC19, 100 pmole each of oligonucleotides M-2161 and M-2177 (SEQ ID NOS:5 and 6, respectively), and the reagents provided in the GENEAMP kit (Perkin Elmer Cetus, Norwalk, Conn.) according to the manufacturer's instructions. The reaction is amplified for nineteen cycles (20 seconds at 94° C., 20 seconds at 50° C., and 30 seconds at 72° C.) followed by a ten minute incubation at 72° C. A 205 bp fragment is isolated by agarose gel electrophoresis.

A DNA sequence encoding the synthetic signal sequence (SEQ ID NO:7) is obtained by PCR amplification of a fragment from plasmid pKFN-1000. Plasmid pKFN-1000 is a derivative of plasmid pTZ19R (Mead et al., *Prot. Engin.* 1: 67–74, 1986) containing a DNA sequence encoding a synthetic yeast signal leader peptide. Plasmid pKFN-1000 is described in WO 90/10075, which is incorporated by reference herein in its entirety. The DNA sequence of the 235 base pairs downstream from the Eco RI site of plasmid pKFN-1000 and the encoded amino acid sequence is shown in SEQ ID NOS: 7 and 8. A 0.7 kb Pvu II fragment of plasmid pKFN-1000 is used as a template. Synthetic oligonucleotide NOR-1478 (SEQ ID NO:9) is identical to a sequence just upstream of the Eco RI site (nucleotides to 1–6 of SEQ ID NO:7). Synthetic oligonucleotide NOR-2523 (SEQ ID NO:10) is complementary to nucleotides 215–235 of the coding sequence in SEQ ID NO:7. A PCR reaction is performed in a 100 µl final volume using 0.1 µg of the 0.7 kb Pvu II fragment, 100 pmoles each of oligonucleotides NOR-1478 and NOR-2523 (SEQ ID NOS: 9 and 10, respectively) and reagents from the GENEAMP commercial kit (Perkin Elmer Cetus) according to the manufacturer's instructions. The PCR reaction is amplified as described above. A 257 bp PCR product is isolated by agarose gel electrophoresis.

A DNA sequence encoding the complete synthetic signal sequence operatively linked to the Kunitz-type inhibitor domain sequence is obtained by amplifying the two PCR fragments described above. A PCR reaction is performed as described above using 100 pmoles each of primers NOR-1478 (SEQ ID NO:9) and M-2177 (SEQ ID NO:6) and 0.1 µg of each of the two PCR fragments described above. The PCR reaction is amplified for sixteen cycles (1 minute at 94° C., 2 minutes at 50° C., 3 minutes at 71° C.) followed by a ten minute incubation at 72° C. A 437 bp fragment is purified by agarose gel electrophoresis. The fragment is then digested with Eco RI and Xba I, and the resulting 408 bp fragment is ligated with plasmid pTZ19R, which had been linearized by digestion with Eco RI and Xba I. The ligation mixture is transformed into competent restriction minus, modification plus *E. coli* strain, and transformants were selected in the presence of ampicillin. Plasmid DNAs prepared from selected. Transformants are sequenced, and a plasmid containing the DNA sequence of the synthetic yeast signal sequence fused to the Kunitz-type inhibitor domain is identified.

The Eco RI-Xba I fragment encoding the secretory signal-Kunitz-type inhibitor domain is then isolated and subcloned into plasmid pMT-636. Plasmid pMT-636 was derived from the shuttle vector pCPOT (Plasmid pCPOT was deposited on May 9, 1984 with the American Type Culture Collection; 12301 Parklawn Dr., Rockville, Md.; under Accession No. 39685) in which the 0.4 kb Hpa I-Nru I fragment containing the *Saccharomyces cerevisiae* LEU2 gene was deleted and, in addition, contains the *Saccharomyces cerevisiae* TPI1 promoter and the TPI1 terminator flanking an Eco RI-Xba I directional cloning site such that the a DNA insert is transcribed in the same direction as the *Schizosaccharomyces pombe* POT1 gene (Norris et al., ibid.). Plasmid pMT-636 has been described in WO 89/01968 and WO 90/10075, which are incorporated herein by reference in their entirety. Plasmid pMT-636 is digested with Nco I and Xba I to isolate the 9.3 kb fragment. Plasmid pMT-636 is also digested with Nco I and Eco RI to obtain the 1.6 kb fragment. The two fragments from pMT-636 are ligated with the Eco RI-Xba I fragment. A plasmid containing the signal sequence-Kunitz-type inhibitor domain fragment in the correct orientation is transformed into *S. cerevisiae* MT-663 (a/αΔtpi/Δtpi pep4-3/pep4-3). Transformants were selected for growth on glucose as the sole carbon source, and cultivated in YEPD media. Transformants are assayed for activity as described in Example 4. The Kunitz-type inhibitor is purified as described in Example 5.

B. Expression of the Kunitz-type Inhibitor Domains of TFPI-2 Comprising Amino Acids 34 through 152 of SEQ ID NO:2

A DNA construct encoding Kunitz-type inhibitor domains of TFPI-2 comprising the amino acid sequence of SEQ ID NO:2 from glutamic acid, amino acid number 34, through lysine, amino acid number 152, is amplified from human genomic DNA as described in Example 1 using oligonucleotide primers M-2161 and M-2162 (SEQ ID NO:5 and SEQ ID NO:11). The resulting PCR-generated fragment is gel-purified and joined to the signal sequence as described above. The plasmid intermediate comprising the synthetic signal sequence and TFPI-2 coding sequence in the vector pTZ19R is used to obtain the signal sequence-TFPI-2fragment for the construction of the yeast expression vector. The Eco RI-Xba I fragment from the plasmid intermediate encoding the signal sequence-TFPI-2 is subcloned into the yeast expression vector MT-636 as described above. A candidate plasmid having the correct insert is transformed into *Saccharomyces cerevisiae* strain MT-663 as described above.

Selected transformants are assayed for activity as described in Example 4. The Kunitz-type inhibitor is purified as described in Example 5.

C. Expression of Kunitz-type Inhibitor Domains of TFPI-2 comprising Amino Acids 34 through 211 of SEQ ID NO:2

A DNA construct encoding Kunitz-type inhibitor domains of TFPI-2 comprising the amino acid sequence of SEQ ID NO:2 from glutamic acid, amino acid number 34, through alanine, amino acid number 211 is constructed by first digesting plasmid pJ-2-11/pUC19 with Bgl II and Hind III to obtain a 528 bp Bgl II-Hind III fragment encoding the three Kunitz-type domains. The Kunitz-type inhibitor domains coding sequence from pJ-2-11/pUC19 is joined to the synthetic signal sequence (SEQ ID NO:7) by replacing the TFPI-2 coding sequence in the plasmid intermediate described in Example 3B. The plasmid intermediate is digested with Bgl II and Xba I to isolate the vector-containing fragment. The Bgl II-Xba I vector. containing fragment is ligated with the Bgl II-Hind III fragment from pJ-2-11/pUC19 and a Hind III-Xba I linker containing a translation stop codon. A plasmid containing the synthetic signal sequence joined in the proper orientation with the TFPI-2 coding sequence is identified.

The Eco RI-Xba I fragment from the plasmid intermediate encoding the signal sequence-TFPI-2 is subcloned into the yeast expression vector MT-636 as described above. A candidate plasmid having the correct insert is transformed into *Saccharomyces cerevisiae* strain MT-663 as described above.

Selected transformants are assayed for activity as described in Example 4. The Kunitz-type inhibitor is purified as described in Example 5.

Example 4

Activity Assays

A. Trypsin inhibitory Activity Assay on Mammalian Cell Culture Supernatants

Conditioned media from cells expressing Kunitz-type inhibitors was assayed for trypsin inhibitor activity. For each clone, 20–100 µl of conditioned medium was added to a solution containing 2.4 µg/ml trypsin (Worthington Biochemical, Freehold, N.J.) in 100 mM NaCl, 50 mM Tris (pH 7.4) to give a final volume of 300 µl. The reactions were incubated at 23° C. for 30 minutes after which 20 µl of 10 mM chromogenic substrate S-2251 (D-Val-Leu-Lys-Nan; Chromogenix, AB, Mindal, Sweden) was added to a final concentration of 0.6 mM. The residual trypsin activity was measured by absorbance at 405 nm.

B. Activity Assay on Yeast Culture Supernatants

Trypsin inhibitory activity is measured on the spent media from cultures of yeast transformants described in Example 3 by diluting 3.2 µl of each spent medium sample with 80 µl of assay buffer (50 mM Tris HCl, pH 7.4, 100 mM NaCl, 2 mM CaCl$_2$, 0.1% w/v PEG 20,000). The diluted supernatant is added to 80 µl of 133 nM bovine trypsin (Novo Nordisk A/S) diluted in assay buffer, and the mixture is incubated for 10 minutes at room temperature. After incubation, 100 µl of 1.8 mM peptidyl nitroanilide substrate S2251 (D-Val-Leu-Lys-Nan; Kabi) diluted in assay buffer is added to each sample, and the samples are incubated with the substrate for 30 minutes. Trypsin inhibitory activity is indicated by a colorless solution. A control reaction, which results in a yellow solution, is produced by a supernatant from a yeast strain not expressing any Kunitz-type inhibitor.

Example 5

Purification of Kunitz-Type Inhibitors

A. Purification of Kunitz-Type Inhibitors from Transfected Mammalian Cell Culture Supernatants Recombinant TFPI-2 was purified from conditioned medium by sequential application of heparin agarose, MONO Q, MONO S and SUPEROSE 12 chromatography as described in more detail below. Approximately five liters of conditioned serum-free media was adjusted to pH 7.5 with 1N NaOH and filtered through a 0.22-µm filter. A 2.6×35 cm heparin sepharose column (Pharmacia Biotech inc., Piscataway, N.J.) was equilibrated at 4° C. with Buffer A (50 mM Tris-HCl (pH 7.5), 10% glycerol). The filtered media was applied to the equilibrated column at a flow rate of 3 ml/min. Following sample application, the column was washed with Buffer A containing 0.2M NaCl. TFPI-2 activity, as judged by its ability to inhibit trypsin (Example 4A), was eluted from the column with Buffer A containing 1M NaCl. The eluent from the heparin sepharose column was dialyzed at 4° C. against 25 mM Tris-HCl (pH 7.5), 10% glycerol. The retentate was subjected to FPLC (Pharmacia Biotech Inc.) on a 5×50 mm column containing an anion exchanger with quaternary amine groups crosslinked to a beaded hydrophylic resin such as a MONO Q (MONO Q HR 5/5; Pharmacia Biotech Inc., Piscataway, N.J.) or the like that had been equilibrated with 25 mM Tris-HCl (pH 7.5), 10% glycerol at room temperature. TFPI-2 was eluted from the column in a linear NaCl gradient (from 0–0.5M NaCl) at a flow rate of 1 ml/min. The TFPI-2 fractions were pooled and dialyzed against 25 mM sodium citrate (pH 5.0), 10% glycerol. The retentate was then subjected to FPLC at room temperature on a 5×50 mm column containing a cation exchanger with charged sulfonic groups coupled to a beaded hydrophylic resin such as MONO S (MONO S HR 5/5, Pharmacia Biotech Inc.) or the like at a flow rate of 0.5 ml/min. TFPI-2 activity was eluted from the MONO S column with a gradient elution from 25 mM sodium citrate (pH 5.0), 10% glycerol to 25 mM Tris-HCl (pH 7.5), 10% glycerol, 1M NaCl. Fractions containing TFPI-2 activity were pooled and concentrated to approximately 1 ml by ultrafiltration. The concentrated samples were subjected to FPLC across a cross-linked agarose gel filtration matrix having a porosity suitable for the separation of proteins from $1×10^3$ to $3×10^5$ MW such as SUPEROSE 12 (Pharmacia Biotech Inc., Piscataway, N.J.) or the like at room temperature in 50 mM Tris-HCl (pH 7.5), 100 mM NaCl. Fractions eluted from the FPLC with TFPI-2 activity were subjected to SDS-PAGE, and pure fractions were pooled and stored at −80° C.

B. Purification of Kunitz-Type Inhibitors from Yeast Culture Supernatants

Kunitz-type inhibitors are purified from yeast culture supernatants essentially as described by Norris et al. (ibid.; which is incorporated herein by reference). Selected transformants are grown in 10 liters of YEPD for approximately 40 hours at 30° C. until an OD$_{600}$ of approximately 25 has been reached. The culture is centrifuged, and the supernatant is decanted.

For purification, a 300 ml-1000 ml aliquot of supernatant is adjusted to pH 2.3 and applied to a column holding 8 ml of S-Sepharaose (Pharmacia-LKB Biotechnology AS, Alleroed, Denmark) that has been previously equilibrated with 20 mM Bicine, pH 8.7 (Sigma Chemical Co., St. Louis, Mo.). After the column has been extensively washed with 20 mM Bicine, pH 8.7, the Kunitz-type inhibitor is eluted with 30 ml of 20 mM Bicine, pH 8.7 containing 1M NaCl. The eluted material is desalted by application to a Sephadex G-25 column (Pharmacia-LKB Biotechnology AS, Alleroed, Denmark; 2.5×30 cm) that has been equilibrated with 20 mM NH$_4$HCO$_3$, pH 7.8. The Kunitz-type inhibitor is eluted with 20 mM NH$_4$HCO$_3$, pH 7.8.

The Kunitz-type inhibitor is further purified and concentrated by chromatography on a Mono S column (Pharmacia-LKB Biotechnology AS, Alleroed, Denmark; 0.5×5 cm) equilibrated with 20 mM Bicine, pH 8.7. After washing with the equilibration buffer at 2 ml/min for 10 minutes, gradient elution of the Kunitz-type inhibitor is carried out over twelve minutes at 1 ml/min from 0–0.6M NaCl in the equilibration buffer. Peak samples are pooled, and the Kunitz-type inhibitor is purified using reverse phase HPLC on a Vydac 214TP510 column (Mikro-lab, Aarhus, Denmark; 1.0×25 cm) with a gradient elution at 4 ml/min from 5% A (0.1% trifluoroacetic acid (TFA) in water) to 45% B (0.7% TFA in acetonitrile) in 20 minutes. The purified product in lyophilized in water, and inhibitor activity is,measured.

Kunitz inhibitor activity is measured using the method essentially described by Norris et al. (ibid.). Briefly, various fixed concentrations of the Kunitz-type inhibitor are incubated in the presence of 0.24 µg/ml of porcine trypsin (Novo Nordisk A/S, Bagsvaerd, Denmark), 12.8 CU/l human plasmin (Kabi, Stockholm, Sweden) or 0.16 nkat/ml human plasma kallikrein (Kabi) in 100 mM NaCl, 50 mM Tris HCl, pH 7.4. After a 30 minute incubation the residual enzymatic activity is measured by the cleavage of a substrate solution containing 0.6 mM of either of the chromogenic peptidyl nitroanilide trypsin/plasmin substrates S2251 (D-Val-Leu-Lys-Nan; Kabi) or S2302 (D-Pro-Phe-Arg-Nan; Kabi) in assay buffer. The samples are incubated for 30 minutes after which the absorbance of each sample is measured at 405 nm. Plasmin or trypsin activity is measured as a decrease in absorbance at 405 nm. From the results, the apparent inhibition constant Ki is calculated.

EXAMPLE 6

Effect of Recombinant TFPI-2 on the Amydolytic Activities of Human Thrombin, Human Factor XA and a Complex of Human Factor VIIA/Tissue Factor.

A. Thrombin amidolytic activity assay

The ability of recombinant TFPI-2 to inhibit the amidolytic activity of human thrombin was determined by a colometric assay using human thrombin (prepared as described by Pedersen, et al., *J. Biol. Chem.* 265: 16786–16793, 1990; which is incorporated by reference herein in its entirety) and various concentrations of recombinant TFPI-2. The assay was set up in a microtiter plate format. Reactions of 200 µl were prepared in the wells of the microtiter plate. The reaction mixtures contained various concentrations of recombinant TFPI-2 and 20 nM human thrombin in 50 mM Tris-HCl (pH 7.5), 0.1% BSA, 5 mM CaC₂. The reactions were incubated at 37° C. for 15 minutes. Following incubation, 50 µl of 10 mM the chromogenic substrate S-2238 (H-D-Phe-Pip-Arg-p-nitroanilide, Chromogenix, AB, Mlndal, Sweden) was added to each well. The absorbance at 405 nm was determined in a kinetic microplate reader (Model UVMAX, Molecular Devices). Recombinant TFPI-2 was shown to have no effect on the amidolytic activity of human thrombin towards S-2238

B. Human Factor Xa Amidolytic Assay

The ability of recombinant TFPI-2 to inhibit the amidolytic activity of factor Xa was determined by a colorimetric assay as described above using 20 nM human factor Xa (prepared as described by Kondo, and Kisiel, *Blood* 70, 1947–1954, 1987; which is incorporated by reference herein in its entirety) in place of the 20 nM human thrombin described above. The reactions were set up and incubated as described above replacing the human thrombin with human factor Xa. Following incubation, 50 µl of 10 mM of the chromogenic substrate S-2222 (Benzoyl-Ile-Glu-Gly-Arg-p-nitroanilide, Chromogenix, AB, Mlndal, Sweden) was added to each well. The absorbance at 405 nm was determined in a kinetic microplate reader (Model UVMAX, Molecular Devices). Recombinant TFPI-2 was shown to weakly inhibit the amidolytic activity of 20 nM factor Xa towards the chromogenic substrate S-2222 in a dose-dependent manner.

Human Factor VIIa/Tissue Factor Amidolytic Assay

The ability of recombinant TFPI-2 to inhibit the amidolytic activity of factor VIIa/tissue factor complex was determined by a colorimetric assay using 70 nM recombinant, truncated, human tissue factor apoprotein consisting of the 219-amino acid extracellular domain (TF$_{1-219}$) (prepared as described by Paborsky, et al., *J. Biol. Chem.* 266: 21911–21916, 1991; which is incorporated herein in its entirety) provided by Gordon Vehar (Genentech Inc., South San Francisco, Calif.), and 20 nM recombinant human factor VIIa (prepared as described by Pedersen, et al., *Biochemistry* 28: 9331–9336, 1989; which is incorporated by reference herein in its entirety) provided by Peter Wildgoose (Novo Nordisk A/S, Bagsvaerd, Denmark) in place of the 20 nM human thrombin described above. The assay was set up and incubated as described above replacing the human thrombin with human factor VIIa and TF$_{1-219}$. Following incubation, 50 µl of 10 mM chromogenic substrate S-2288 (H-D-Ile-Pro-Arg-p-nitroanilide, Chromogenix, AB) was added to each well. The absorbance at 405 nm was determined in a kinetic microplate reader (Model UVMAX, Molecular Devices). Recombinant TFPI-2 was shown to inhibit the amidolytic activity of 20 nM factor VIIa-tissue factor towards the chromogenic substrate S-2288 in a dose-dependent manner.

Example 7

Amino Acid Sequence Analysis

Automated amino acid sequencing was performed in a gas vapor sequenator (Beckman Instruments; Model LF 3000 or the like) equipped with an on-line phenylthiohydantoin analyzer. The phenylthiohydantoin peaks were integrated using SYSTEM GOLD software provided with the sequenator. Approximately 100 picomoles of protein were subjected to sequence analysis. Amino-terminal amino acid sequence analysis of a single preparation of recombinant TFPI-2 indicated a major sequence (~70%) of Asp-Ala-Ala-Gln-Glu-Pro-Thr-Gly-Asn-Asn (SEQ ID NO:12) and a minor sequence (~30%) of Ala-Gln-Glu-Pro-Thr-Gly-Asn-Asn (SEQ ID NO:13), suggesting either alternative cleavage sites by the signal peptidase, or possible amino-terminal degradation by exopeptidases during its purification.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for inhibiting blood coagulation in a mammal comprising administering a human Kunitz-type inhibitor wherein said Kunitz-type inhibitor is an isolated human Kunitz-type inhibitor comprising the amino acid sequence of SEQ ID NO:15 wherein each Xaa is individually any amino acid except cysteine and said isolated human Kunitz-type inhibitor has both an amino-terminal end and a carboxy-terminal end, in an amount sufficient to inhibit blood coagulation.

2. A method for inhibiting blood coagulation in a mammal according to claim 1 wherein said Kunitz-type inhibitor comprises the amino acid sequence of an amino acid sequence selected from the group consisting of SEQ ID NO:2 from methionine, amino acid 1 to phenylalanine, amino acid number 235; the amino acid sequence of SEQ ID NO:2 from glutamic acid, amino acid number 34 to isoleucine, amino acid number 89; the amino acid sequence of SEQ ID NO:2 from glutamic acid, amino acid 34 to lysine, amino acid 152 and the amino acid sequence of SEQ ID NO:2 from glutamic acid, amino acid number 34 to alanine, amino acid number 211.

3. A method for inhibiting blood coagulation in a mammal according to claim 1 wherein said Kunitz-type inhibitor further comprises the amino acid sequence of SEQ ID NO:12 or SEQ ID NO:13 at its amino-terminal end.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 979 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens
        ( F ) TISSUE TYPE: Placenta ( v i i ) IMMEDIATE SOURCE:
        ( B ) CLONE: J-2-11

( i x ) FEATURE:
        ( A ) NAME/KEY: CDS
        ( B ) LOCATION: 39..746

( x i ) SEQUENCE DESCRIPTION: SEQ ID NO:1:

```
GGACGCCTTG CCCAGCGGGC CGCCCGACCC CCTGCACC ATG GAC CCC GCT CGC                53
                                          Met Asp Pro Ala Arg
                                          1               5

CCC CTG GGG CTG TCG ATT CTG CTG CTT TTC CTG ACG GAG GCT GCA CTG              101
Pro Leu Gly Leu Ser Ile Leu Leu Leu Phe Leu Thr Glu Ala Ala Leu
            10                  15                  20

GGC GAT GCT GCT CAG GAG CCA ACA GGA AAT AAC GCG GAG ATC TGT CTC              149
Gly Asp Ala Ala Gln Glu Pro Thr Gly Asn Asn Ala Glu Ile Cys Leu
            25                  30                  35

CTG CCC CTA GAC TAC GGA CCC TGC CGG GCC CTA CTT CTC CGT TAC TAC              197
Leu Pro Leu Asp Tyr Gly Pro Cys Arg Ala Leu Leu Leu Arg Tyr Tyr
        40                  45                  50

TAC GAC AGG TAC ACG CAG AGC TGC CGC CAG TTC CTG TAC GGG GGC TGC              245
Tyr Asp Arg Tyr Thr Gln Ser Cys Arg Gln Phe Leu Tyr Gly Gly Cys
        55                  60                  65

GAG GGC AAC GCC AAC AAT TTC TAC ACC TGG GAG GCT TGC GAC GAT GCT              293
Glu Gly Asn Ala Asn Asn Phe Tyr Thr Trp Glu Ala Cys Asp Asp Ala
70                  75                  80                  85

TGG AGG ATA GAA AAA GTT CCC AAA GTT TGC CGG CTG CAA GTG AGT              341
Cys Trp Arg Ile Glu Lys Val Pro Lys Val Cys Arg Leu Gln Val Ser
            90                  95                  100

GTG GAC GAC CAG TGT GAG GGG TCC ACA GAA AAG TAT TTC TTT AAT CTA              389
Val Asp Asp Gln Cys Glu Gly Ser Thr Glu Lys Tyr Phe Phe Asn Leu
            105                 110                 115

AGT TCC ATG ACA TGT GAA AAA TTC TTT TCC GGT GGG TGT CAC CGG AAC              437
Ser Ser Met Thr Cys Glu Lys Phe Phe Ser Gly Gly Cys His Arg Asn
            120                 125                 130

CGG ATT GAG AAC AGG TTT CCA GAT GAA GCT ACT TGT ATG GGC TTC TGC              485
Arg Ile Glu Asn Arg Phe Pro Asp Glu Ala Thr Cys Met Gly Phe Cys
    135                 140                 145

GCA CCA AAG AAA ATT CCA TCA TTT TGC TAC AGT CCA AAA GAT GAG GGA              533
Ala Pro Lys Lys Ile Pro Ser Phe Cys Tyr Ser Pro Lys Asp Glu Gly
150                 155                 160                 165

CTG TGC TCT GCC AAT GTG ACT CGC TAT TAT TTT AAT CCA AGA TAC AGA              581
Leu Cys Ser Ala Asn Val Thr Arg Tyr Tyr Phe Asn Pro Arg Tyr Arg
            170                 175                 180

ACC TGT GAT GCT TTC ACC TAT ACT GGC TGT GGA GGG AAT GAC AAT AAC              629
Thr Cys Asp Ala Phe Thr Tyr Thr Gly Cys Gly Gly Asn Asp Asn Asn
            185                 190                 195

TTT GTT AGC AGG GAG GAT TGC AAA CGT GCA TGT GCA AAA GCT TTG AAA              677
Phe Val Ser Arg Glu Asp Cys Lys Arg Ala Cys Ala Lys Ala Leu Lys
            200                 205                 210

AAG AAA AAG AAG ATG CCA AAG CTT CGC TTT GCC AGT AGA ATC CGG AAA              725
Lys Lys Lys Lys Met Pro Lys Leu Arg Phe Ala Ser Arg Ile Arg Lys
            215                 220                 225

ATT CGG AAG AAG CAA TTT TAAACATTCT TAATATGTCA TCTTGTTTGT                     773
Ile Arg Lys Lys Gln Phe
230                 235

CTTTATGGCT TATTGCCTT  TATGGTTGTA TCTGAAGAAT AATATGACAG CATGAGGAAA            833

CAAATCATTG GTGATTTATT CACCAGTTTT TATTAATACA AGTCACTTTT TCAAAAATTT            893

GGATTTTTTT ATATATAACT AGCTGCTATT CAAATGTGAG TCTACCATTT TTAATTTATG            953

GTTCAACTGT TTGTGAGACT GAATTC                                                 979
```

( 2 ) INFORMATION FOR SEQ ID NO:2:

( i ) SEQUENCE CHARACTERISTICS:
        ( A ) LENGTH: 235 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Asp | Pro | Ala | Arg | Pro | Leu | Gly | Leu | Ser | Ile | Leu | Leu | Leu | Phe | Leu |
| 1 | | | | 5 | | | | 10 | | | | | | 15 | |
| Thr | Glu | Ala | Ala | Leu | Gly | Asp | Ala | Ala | Gln | Glu | Pro | Thr | Gly | Asn | Asn |
| | | | 20 | | | | | 25 | | | | | 30 | | |
| Ala | Glu | Ile | Cys | Leu | Leu | Pro | Leu | Asp | Tyr | Gly | Pro | Cys | Arg | Ala | Leu |
| | | 35 | | | | | 40 | | | | | 45 | | | |
| Leu | Leu | Arg | Tyr | Tyr | Tyr | Asp | Arg | Tyr | Thr | Gln | Ser | Cys | Arg | Gln | Phe |
| | 50 | | | | | 55 | | | | | 60 | | | | |
| Leu | Tyr | Gly | Gly | Cys | Glu | Gly | Asn | Ala | Asn | Asn | Phe | Tyr | Thr | Trp | Glu |
| 65 | | | | | 70 | | | | | 75 | | | | | 80 |
| Ala | Cys | Asp | Asp | Ala | Cys | Trp | Arg | Ile | Glu | Lys | Val | Pro | Lys | Val | Cys |
| | | | | 85 | | | | | 90 | | | | | 95 | |
| Arg | Leu | Gln | Val | Ser | Val | Asp | Asp | Gln | Cys | Glu | Gly | Ser | Thr | Glu | Lys |
| | | | | 100 | | | | | 105 | | | | | 110 | |
| Tyr | Phe | Phe | Asn | Leu | Ser | Ser | Met | Thr | Cys | Glu | Lys | Phe | Phe | Ser | Gly |
| | | 115 | | | | | 120 | | | | | 125 | | | |
| Gly | Cys | His | Arg | Asn | Arg | Ile | Glu | Asn | Arg | Phe | Pro | Asp | Glu | Ala | Thr |
| | 130 | | | | | 135 | | | | | 140 | | | | |
| Cys | Met | Gly | Phe | Cys | Ala | Pro | Lys | Lys | Ile | Pro | Ser | Phe | Cys | Tyr | Ser |
| 145 | | | | | 150 | | | | | 155 | | | | | 160 |
| Pro | Lys | Asp | Glu | Gly | Leu | Cys | Ser | Ala | Asn | Val | Thr | Arg | Tyr | Tyr | Phe |
| | | | | 165 | | | | | 170 | | | | | 175 | |
| Asn | Pro | Arg | Tyr | Arg | Thr | Cys | Asp | Ala | Phe | Thr | Tyr | Thr | Gly | Cys | Gly |
| | | | 180 | | | | | 185 | | | | | 190 | | |
| Gly | Asn | Asp | Asn | Asn | Phe | Val | Ser | Arg | Glu | Asp | Cys | Lys | Arg | Ala | Cys |
| | | 195 | | | | | 200 | | | | | 205 | | | |
| Ala | Lys | Ala | Leu | Lys | Lys | Lys | Lys | Met | Pro | Lys | Leu | Arg | Phe | Ala | |
| | 210 | | | | 215 | | | | | 220 | | | | | |
| Ser | Arg | Ile | Arg | Lys | Ile | Arg | Lys | Lys | Gln | Phe | | | | | |
| 225 | | | | | 230 | | | | | 235 | | | | | |

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC4792

( x i ) SEQUENCE DESCRIPTION: SEQ ID NO:3:

GTTGTTGCTG TTGCCTCCGC AGCCTCCGTA        30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: ZC6281

( x i ) SEQUENCE DESCRIPTION: SEQ ID NO:4:

```
ACAGATCTCC GCGTTATTTC CTGTTGGCTC                                              30
```

( 2 ) INFORMATION FOR SEQ ID NO:5:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( v i i ) IMMEDIATE SOURCE:
    ( B ) CLONE: M-2161

( x i ) SEQUENCE DESCRIPTION: SEQ ID NO:5:

```
GCTGAGAGAT TGGAGAAGAG AGAGATCTGT CTCCTGCC                                     38
```

( 2 ) INFORMATION FOR SEQ ID NO:6:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( v i i ) IMMEDIATE SOURCE:
    ( B ) CLONE: M-2177

( x i ) SEQUENCE DESCRIPTION: SEQ ID NO:6:

```
GAAACCTCTA GACTTATATC CTCCAGCAAG CATC                                         34
```

( 2 ) INFORMATION FOR SEQ ID NO:7:

( i ) SEQUENCE CHARACTERISTICS:
    ( A ) LENGTH: 235 base pairs
    ( B ) TYPE: nucleic acid
    ( C ) STRANDEDNESS: single
    ( D ) TOPOLOGY: linear ( i x ) FEATURE:
    ( A ) NAME/KEY: CDS
    ( B ) LOCATION: 77..235

( x i ) SEQUENCE DESCRIPTION: SEQ ID NO:7:

```
GAATTCCATT CAAGAATAGT TCAAACAAGA AGATTACAAA CTATCAATTT CATACACAAT             60

ATAAACGACC AAAAGA ATG AAG GCT GTT TTC TTG GTT TTG TCC TTG ATC                109
                  Met Lys Ala Val Phe Leu Val Leu Ser Leu Ile
                   1               5                  10

GGA TTC TGC TGG GCC CAA CCA GTC ACT GGC GAT GAA TCA TCT GTT GAG              157
Gly Phe Cys Trp Ala Gln Pro Val Thr Gly Asp Glu Ser Ser Val Glu
             15                  20                  25

ATT CCG GAA GAG TCT CTG ATC ATC GCT GAA AAC ACC ACT TTG GCT AAC              205
Ile Pro Glu Glu Ser Leu Ile Ile Ala Glu Asn Thr Thr Leu Ala Asn
         30                  35                  40

GTC GCC ATG GCT GAG AGA TTG GAG AAG AGA                                      235
Val Ala Met Ala Glu Arg Leu Glu Lys Arg
         45                  50
```

( 2 ) INFORMATION FOR SEQ ID NO:8:

( i ) SEQUENCE CHARACTERISTICS:
    ( A ) LENGTH: 53 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

```
Met Lys Ala Val Phe Leu Val Leu Ser Leu Ile Gly Phe Cys Trp Ala
```

```
             1               5                      10                        15
Gln Pro Val Thr Gly Asp Glu Ser Ser Val Glu Ile Pro Glu Glu Ser
            20                      25                    30

Leu Ile Ile Ala Glu Asn Thr Thr Leu Ala Asn Val Ala Met Ala Glu
            35                      40                    45

Arg Leu Glu Lys Arg
            50
```

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: NOR-1478

( x i ) SEQUENCE DESCRIPTION: SEQ ID NO:9:

GTAAAACGAC GGCCAGT                          17

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: NOR-2523

( x i ) SEQUENCE DESCRIPTION: SEQ ID NO:10:

TCTCTTCTCC AATCTCTCAG C                    21

( 2 ) INFORMATION FOR SEQ ID NO:11:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( v i i ) IMMEDIATE SOURCE:
        ( B ) CLONE: M-2162

( x i ) SEQUENCE DESCRIPTION: SEQ ID NO:11:

CTTTTACTCT AGACTTACTT TGGTGCGCAG AAGCC        35

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:12:

```
Asp Ala Ala Gln Glu Pro Thr Gly Asn Asn
 1               5                   10
```

( 2 ) INFORMATION FOR SEQ ID NO:13:

( i ) SEQUENCE CHARACTERISTICS:

(A) LENGTH: 8 amino acids
(B) TYPE: amino acid
(D) TOPOLOGY: linear (v) FRAGMENT TYPE: N-terminal (xi) SEQUENCE DESCRIPTION: SEQ ID NO:13:

Ala Gln Glu Pro Thr Gly Asn Asn
1               5

(2) INFORMATION FOR SEQ ID NO:14:

(i) SEQUENCE CHARACTERISTICS:
  (A) LENGTH: 165 base pairs
  (B) TYPE: nucleic acid
  (C) STRANDEDNESS: single
  (D) TOPOLOGY: linear (ix) FEATURE:
  (A) NAME/KEY: CDS
  (B) LOCATION: 1..165

(ix) FEATURE:
  (A) NAME/KEY: -
  (B) LOCATION: 1..3
  (D) OTHER INFORMATION: /label=Codon-1
      / note= "wherein the nucleotide triplet 1-3 encodes
      any amino acid except cysteine"

(ix) FEATURE:
  (A) NAME/KEY: -
  (B) LOCATION: 4..6
  (D) OTHER INFORMATION: /label=Codon-2
      / note= "wherein the nucleotide triplet 4-6 encodes
      any amino acid except cysteine"

(ix) FEATURE:
  (A) NAME/KEY: -
  (B) LOCATION: 160..162
  (D) OTHER INFORMATION: /label=codon-54
      / note= "wherein the nucleotide triplet 160-162
      encodes any amino acid except cysteine"

(ix) FEATURE:
  (A) NAME/KEY: -
  (B) LOCATION: 163..165
  (D) OTHER INFORMATION: /label=Codon-55
      / note= "wherein the nucleotide triplet 112-114
      encodes any amino acid except cysteine"

(xi) SEQUENCE DESCRIPTION: SEQ ID NO:14:

```
NNNNNNTGTC TCCTGCCCCT AGACTACGGA CCCTGCCGGG CCCTACTTCT CCGTTACTAC     60
TACGACAGGT ACACGCAGAG CTGCCGCCAG TTCCTGTACG GGGCTGCGA GGGCAACGCC     120
AACAATTTCT ACACCTGGGA GGCTTGCGAC GATGCTTGCN NNNN                     165
```

(2) INFORMATION FOR SEQ ID NO:15:

(i) SEQUENCE CHARACTERISTICS:
  (A) LENGTH: 55 amino acids
  (B) TYPE: amino acid
  (D) TOPOLOGY: linear (v) FRAGMENT TYPE: internal (ix) FEATURE:
  (A) NAME/KEY: Region
  (B) LOCATION: 1..2
  (D) OTHER INFORMATION: /label=aa1-2
      / note= "wherein each amino acid from position 1 to
      2 is individually any amino acid except cysteine"

(ix) FEATURE:
  (A) NAME/KEY: Region
  (B) LOCATION: 54..55

(D) OTHER INFORMATION: /label=aa54-55
/ note= "wherein each amino acid from postion 54 to
55 is individually any amino acid except cysteine"

(xi) SEQUENCE DESCRIPTION: SEQ ID NO:15:

| Xaa | Xaa | Cys | Leu | Leu | Pro | Leu | Asp | Tyr | Gly | Pro | Cys | Arg | Ala | Leu | Leu |
| 1 | | | | 5 | | | | | 10 | | | | | 15 | |

| Leu | Arg | Tyr | Tyr | Tyr | Asp | Arg | Tyr | Thr | Gln | Ser | Cys | Arg | Gln | Phe | Leu |
| | | | 20 | | | | | 25 | | | | | 30 | | |

| Tyr | Gly | Gly | Cys | Glu | Gly | Asn | Ala | Asn | Asn | Phe | Tyr | Thr | Trp | Glu | Ala |
| | | 35 | | | | | 40 | | | | | 45 | | | |

| Cys | Asp | Asp | Ala | Cys | Xaa | Xaa |
| | 50 | | | | | 55 |